United States Patent [19]

Wilhelm

[11] 3,966,895

[45] June 29, 1976

[54] DEHYDROGENATION WITH A NONACIDIC MULTIMETALLIC CATALYST

[75] Inventor: Frederick C. Wilhelm, Arlington Heights, Ill.

[73] Assignee: Universal Oil Products Company, Des Plaines, Ill.

[22] Filed: Aug. 27, 1974

[21] Appl. No.: 501,113

Related U.S. Application Data

[63] Continuation-in-part of Ser. No. 348,379, April 5, 1973, abandoned, which is a continuation-in-part of Ser. No. 81,512, Oct. 16, 1970, abandoned, which is a continuation-in-part of Ser. No. 15,960, March 2, 1970, abandoned.

[52] U.S. Cl. .................. 260/668 D; 260/669 R; 260/683.3
[51] Int. Cl.² ............................................ C07C 5/18
[58] Field of Search............ 260/668 D, 669, 683.3; 208/138

[56] References Cited
UNITED STATES PATENTS

| | | | |
|---|---|---|---|
| 2,981,696 | 4/1961 | Hervert et al. | 252/466 B |
| 3,025,247 | 3/1962 | Oleck | 252/466 B |
| 3,094,493 | 6/1963 | Nixon | 252/466 B |
| 3,177,160 | 4/1965 | de Rosset | 252/466 B |
| 3,647,719 | 3/1972 | Hayes | 252/466 PT |
| 3,755,481 | 8/1973 | Hayes | 260/668 D |
| 3,851,003 | 11/1974 | Wilhelm | 260/668 D |

*Primary Examiner*—C. Davis
*Attorney, Agent, or Firm*—James R. Hoatson, Jr.; Thomas K. McBride; William H. Page, II

[57] ABSTRACT

A dehydrogenatable hydrocarbon is dehydrogenated by contacting the hydrocarbon, hydrogen, and water or a water-producing substance, at dehydrogenation conditions, with a nonacidic catalytic composite comprising a combination of catalytically effective amounts of a platinum group metal component, a nickel component, a Group IVA metallic component, and an alkali or alkaline earth component with a porous carrier material. A specific example of the nonacidic, multimetallic catalytic composite disclosed herein is a combination of a platinum metal component, a nickel component, a germanium component, and an alkali or alkaline earth component with an alumina carrier material. The amounts of the catalytically active components contained in this last composite are, on an elemental basis, 0.01 to 2 wt. % platinum, 0.01 to 5 wt. % nickel, 0.01 to 5 wt. % germanium, and 0.1 to 5 wt. % of the alkali or alkaline earth metal.

24 Claims, No Drawings

DEHYDROGENATION WITH A NONACIDIC MULTIMETALLIC CATALYST

CROSS-REFERENCES TO RELATED APPLICATIONS

This application is a continuation-in-part of my prior, copending application Ser. No. 348,379, filed Apr. 5, 1973, and now abandoned, which is in turn a continuation-in-part of my prior, now abandoned, application Ser. No. 81,512, filed Oct. 16, 1970, and which in turn is a continuation-in-part of my prior, now abandoned application Ser. No. 15,960, filed Mar. 2, 1970. A related application is my prior application Ser. No. 303,470, filed Nov. 3, 1972, and now U.S. Pat. No. 3,825,612. All of the teachings of these prior applications are specifically incorporated herein by references.

The subject of the present invention is, broadly an improved method for dehydrogenating a dehydrogenatable hydrocarbon to produce a product hydrocarbon containing the same number of carbon atoms but fewer hydrogen atoms. In a narrower aspect, the present invention is a method of dehydrogenating normal paraffin hydrocarbons containing 4 to 30 carbon atoms per molecule to the corresponding normal mono-olefins with minimum production of side products. Another aspect of the present invention involves a novel nonacidic, multimetallic catalytic composite comprising a combination of catalytically effective amounts of a platinum group metal component, a nickel component, a Group IVA metallic component, and an alkali or alkaline earth metal component with a porous carrier material. This composite has highly preferred characteristics of activity, selectivity, and stability when it is employed in the dehydrogenation of dehydrogenatable hydrocarbons such as aliphatic hydrocarbons, naphthenic hydrocarbons, and alkylaromatic hydrocarbons.

The dehydrogenation of dehydrogenatable hydrocarbons is an important commercial process because of the great and expanding demand for dehydrogenated hydrocarbons for use in the manufacture of various chemical products such as detergents, plastics, synthetic rubbers, pharmaceutical products, high octane gasoline, perfumes, drying oils, ion-exchange resins, and various other products well known to those skilled in the art. One example of this demand is in the manufacture of high octane gasoline by using $C_3$ and $C_4$ mono-olefins to alkylate isobutane. A second example is the greatly increased requirements of the petrochemical industry for the production of aromatic hydrocarbons from the naphthene component of petroleum. Another example of this demand is in the area of dehydrogenation of normal paraffin hydrocarbons to produce normal mono-olefins having 4 to 30 carbon atoms per molecule. These normal mono-olefins can, in turn, be utilized in the synthesis of vast numbers of other chemical products. For example, derivatives of normal mono-olefins have become of substantial importance to the detergent industry where they are utilized to alkylate an alkylatable aromatic such as benzene, with subsequent transformation of the product arylalkane into a wide variety of biodegradable detergents such as the alkylaryl sulfonate type of detergent which is most widely used today for household, industrial, and commercial purposes. Still another large class of detergents produced from these normal mono-olefins are the oxyalkylated phenol derivatives in which the alkyl phenol base is prepared by the alkylation of phenol with these normal mono-olefins. Yet another type of detergent produced from these normal mono-olefins is a biodegradable alkylsulfate formed by the direct sulfation of the normal mono-olefin. Likewise, the olefin can be subjected to direct sulfonation to make biodegradable alkenylsulfonates. As a further example, these mono-olefins can be hydrated to produce alcohols which then, in turn, can be used to produce plasticizers, synthetic lube oils, and the like products.

Regarding the use of products made by the dehydrogenation of alkylaromatic hydrocarbons, these find wide application in industries including the petroleum, petrochemical, pharmaceutical, detergent, plastic industries, and the like. For example, ethylbenzene is dehydrogenated to produce styrene which is utilized in the manufacturing of polystyrene plastics, styrene-butadiene rubber, and the like products. Isopropylbenzene is dehydrogenated to form alphamethyl styrene which, in turn, is extensively used in polymer formation and in the manufacture of drying oils, ion-exchange resins and the like material.

Responsive to this demand for these dehydrogenation products, the art has developed a number of alternative methods to produce them in commercial quantities. One method that is widely utilized involves the selective dehydrogenation of dehydrogenatable hydrocarbons by contacting the hydrocarbons with a suitable catalyst at dehydrogenation conditions. As is the case with most catalytic procedures, the principal measure of effectiveness for this dehydrogenation method involves the ability to perform its intended function with minimum interference of side reactions for extended periods of time. The analytical terms used in the art to broadly measure how well a particular catalyst performs its intended functions in a particular hydrocarbon conversion reaction are activity, selectivity, and stability, and for purposes of discussion here, these terms are generally defined for a given reactant as follows: (1) activity is a measure of the catalyst's ability to convert the hydrocarbon reactant into products at a specified severity level where severity level means the conditions used-- that is, the temperature, pressure, contact time, and presence of diluents such as $H_2$; (2) selectivity usually refers to the amount of desired product or products obtained relative to the amount of the reactant charged or converted; (3) stability refers to the rate of change with time of the activity and selectivity parameters—obviously the smaller rate implying the more stable catalyst. More specifically, in a dehydrogenation process, activity commonly refers to the amount of conversion that takes place for a given dehydrogenatable hydrocarbon at a specified severity level and is typically measured on the basis of disappearance of the dehydrogenatable hydrocarbon; selectivity is typically measured by the amount, calculated on a mole percent of converted dehydrogenatable hydrocarbon basis, of the desired dehydrogenated hydrocarbon obtained at the particular activity or severity level; and stability is typically equated to the rate of change with time of activity as measured by disappearance of the dehydrogenatable hydrocarbon and of selectivity as measured by the amount of desired hydrocarbon produced. Accordingly, the major problem facing workers in the hydrocarbon dehydrogenation art is the development of a more active and selective catalytic composite that has good stability characteristics.

I have now found a multimetallic catalytic composite which possesses improved activity, selectivity, and stability when it is employed in a process for the dehydrogenation of dehydrogenatable hydrocarbons. In particular, I have determined that a superior dehydrogenation catalyst comprises a nonacidic combination of catalytically effective amounts of a platinum group component, a nickel component, a Group IVA metallic component, and an alkali or alkaline earth component with a porous carrier material in a manner such that the components are uniformly dispersed throughout the porous carrier material, the platinum group metal is reduced to the elemental state and the Group IVA metal and the alkali or alkaline earth metals are present in a positive oxidation state. This catalyst can, in turn, enable the performance of a dehydrogenation process to be substantially improved. Moreover, particularly good results are obtained when this multimetallic catalyst is utilized in the dehydrogenation of long chain normal paraffins to produce the corresponding normal mono-olefins with minimization of side reactions such as skeletal isomerization, aromatization, and cracking. In sum, the current invention involves the significant finding that a combination of a nickel component and a Group IVA metallic component can be utilized to beneficially interact with a platinum-containing dehydrogenation catalyst if the metal moieties are uniformly dispersed in the catalyst and if their oxidation states are controlled as hereinafter specified.

It is, accordingly, one object of the present invention to provide a novel method for dehydrogenation of dehydrogenatable hydrocarbons utilizing a multimetallic catalytic composite containing a platinum group metal component, a nickel component, a Group IVA metallic component, and an alkali or alkaline earth component combined with a porous carrier material. A second object is to provide a novel nonacidic catalytic composite having superior performance characteristics when utilized in a dehydrogenation process. Another object is to provide an improved method for the dehydrogenation of normal paraffin hydrocarbons to produce normal mono-olefins. Yet another object is to improve the performance of a nonacidic platinum-containing dehydrogenation catalyst by using a combination of relatively inexpensive components, nickel and a Group IVA metal, to beneficially interact and promote the platinum metal.

In brief summary, one embodiment of the present invention involves a nonacidic catalytic composite comprising a porous carrier material containing, on an elemental basis, about 0.01 to about 2 wt. % platinum group metal, about 0.01 to about 5 wt. % nickel, about 0.01 to about 5 wt. % Group IVA metal, and about 0.1 to about 5 wt. % of an alkali or alkaline earth metal, wherein the platinum group metal, Group IVA metal, nickel, and alkali or alkaline earth metal are uniformly dispersed throughout the porous carrier material, wherein substantially all of the platinum group metal is present in the elemental metallic state, wherein substantially all of the Group IVA metal is present in an oxidation state above that of the elemental metal, and wherein substantially all of the alkali or alkaline earth metal is present in an oxidation state above that of the elemental metal.

A second embodiment of the instant invention relates to a method of dehydrogenation of a dehydrogenatable hydrocarbon comprising contacting the hydrocarbon, hydrogen, and water or a water-producing substance, at dehydrogenation conditions, with a nonacidic catalytic composite comprising a porous carrier material containing, on an elemental basis, about 0.01 to about 2 wt. % platinum group metal, about 0.01 to about 5 wt. % nickel, about 0.01 to about 5 wt. % Group IVA metal, and about 0.1 to about 5 wt. % alkali or alkaline earth metal, wherein the platinum group metal, Group IVA metal, nickel, and alkaline earth metal are uniformly dispersed throughout the porous carrier material, wherein substantially all of the platinum group metal is present in the elemental metallic state, wherein substantially all of the Group IVA metal is present in an oxidation state above that of the elemental metal, and wherein substantially all of the alkali or alkaline earth metal is present in an oxidation state above that of the elemental metal.

A third embodiment comprehends a method for dehydrogenating a dehydrogenatable hydrocarbon as described above in the second embodiment wherein the amount of water or water-producing substance corresponds to about 50 to about 10,000 wt. ppm. of the hydrocarbon charge.

Another embodiment involves a method for the selective dehydrogenation of a normal paraffin hydrocarbon containing about 4 to 30 carbon atoms per molecule to the corresponding normal mono-olefins. The method essentially involving contacting the normal paraffin hydrocarbons, hydrogen, and water or a water-producing substance at dehydrogenation conditions with a catalytic composite defined in the first embodiment.

Other objects and embodiments of the present invention include specific details regarding essential and preferred ingredients of the disclosed multimetallic catalytic composite, preferred amounts of ingredients for this composite, suitable methods of composite preparation, dehydrogenatable hydrocarbons that are preferably used with this catalyst in a dehydrogenation process, operating conditions that can be utilized with this catalyst in a dehydrogenation process and the like particulars. These objects and embodiments are disclosed in the following detailed explanation of the various technical aspects of the present invention. It is to be noted that: (1) the terms "catalyst" and "catalytic composite" are used herein in an equivalent and interchangeable manner; (2) the expression "uniformly dispersed throughout a carrier material" is intended to mean that the amount of the component is approximately the same in any reasonably divisible portion of the carrier material; and, (3) the term "nonacidic" means that the catalyst produces less than 10% conversion of 1-butene to isobutylene when tested at dehydrogenation conditions, and preferably less than 1%.

Regarding the dehydrogenatable hydrocarbon that is subjected to the instant method, it can, in general, be an organic compound having 2 to 30 carbon atoms per molecule and containing at least 1 pair of adjacent carbon atoms having hydrogen attached thereto. That is, it is intended to include within the scope of the present invention the dehydrogenation of any organic compound capable of being dehydrogenated to produce products containing the same number of carbon atoms but fewer hydrogen atoms, and capable of being vaporized at the dehydrogenation conditions used herein. More particularly, suitable dehydrogenatable hydrocarbons are: aliphatic compounds containing 2 to 30 carbon atoms per molecule, alkylaromatic hydrocarbons where the alkyl group contains 2 to 6 carbon atoms, and naphthenes or alkyl-substituted naphthenes. Specific examples of suitable dehydrogenatable hydrocarbons are: (1) alkanes such as ethane, propane, n-butane, isobutanes, n-pentane, isopentane, n-hexane, 2-methylpentane, 2,2-dimethylbutane, n-heptane, n-octane, 2-methylhexane, 2,2,3-trimethylbutane, and the like compounds; (2) naphthenes such as cyclopentane, methylcyclopentane, ethylcyclopentane, n-propylcyclopentane, cyclohexane, isopropylcyclopentane, 1,3-dimethylcyclohexane, and the like compounds; and (3) alkylaromatics such as ethylbenzene, n-propylbenzene, n-butylbenzene, 1,3,5-triethylbenzene, isopropylbenzene, isobutylbenzene, ethylnaphthalene, and the like compounds.

In a preferred embodiment, the dehydrogenatable hydrocarbon is a normal paraffin hydrocarbon having about 4 to about 30 carbon atoms per molecule. For example, normal paraffin hydrocarbons containing about 10 to 18 carbon atoms per molecule are dehydrogenated by the subject method to produce the corresponding normal mono-olefin which can, in turn, be alkylated with benzene and sulfonated to make alkylbenzene sulfonate detergents having superior biodegradability. Likewise, n-alkanes having 10 to 18 carbon atoms per molecule can be dehydrogenated to the corresponding normal mono-olefin which, in turn, can be sulfated or sulfonated to make excellent detergents. Similarly, n-alkanes having 6 to 10 carbon atoms per molecule can be dehydrogenated to form the corresponding monoolefins which can, in turn, be hydrated to produce valuable alcohols. Preferred feed streams for the manufacture of detergent intermediates contain a mixture of 4 or 5 adjacent normal paraffin homologues such as $C_{10}$ to $C_{13}$, $C_{11}$ to $C_{14}$, $C_{11}$ to $C_{15}$, and the like mixtures.

An essential feature of the present invention involves the use of a nonacidic, multimetallic catalytic composite comprising a combination of catalytically effective amounts of a platinum group component, a nickel component, a Group IVA metallic component, and an alkali or alkaline earth component with a porous carrier material.

Considering first the porous carrier material, it is preferred that the material be a porous, adsorptive, high surface area support having a surface area of about 25 to about 500 m²/g. The porous carrier material should be relatively refractory to the conditions utilized in the dehydrogenation process and it is intended to include within the scope of the present invention carrier material which have traditionally been utilized in hydrocarbon conversion catalysts such as: (1) activated carbon, coke, or charcoal; (2) silica or silica gel, silicon carbide, clays, and silicates including those synthetically prepared and naturally occurring, which may or may not be acid treated, for example, attapulgus clay, china clay, diatomaceous earth, fuller's earth, kaolin, kieselguhr, etc.; (3) ceramics, procelain, crushed firebrick, bauxite; (4) refractory inorganic oxides such as alumina, titanium dioxide, zirconium dioxide, chromium oxide, zinc oxide, magnesia, thoria, boria, silica-alumina, silica magnesia, chromia-alumina, alumina-boria, silica-zirconia, etc.; (5) zeolitic crystalline aluminosilicates such as naturally occurring or synthetically prepared mordenite and/or faujasite, either in the hydrogen form or in a form which has been treated with multivalent cations; and, (6) combination of elements from one or more of these groups. The preferred porous carrier materials for use in the present invention are refractory inorganic oxides, with best results obtained with an alumina carrier material. Suitable alumina materials are the crystalline aluminas known as the gamma-, eta-, and theta-aluminas, with gamma-alumina giving best results. In addition, in some embodiments, the alumina carrier material may contain minor proportions of other well known refractory inorganic oxides such as silica, zirconia, magnesia, etc.; however, the preferred support is substantially pure gamma-alumina. Preferred carrier materials have an apparent bulk density of about 0.3 to about 0.7 g/cc and surface area characteristics such that the average pore diameter is about 20 to 300 Angstroms, the pore volume is about 0.1 to about 1 cc/g and the surface area is about 100 to about 500 m²/g. In general, excellent results are typically obtained with a gamma-alumina carrier material which is used in the form of spherical particles having: a relatively small diameter (i.e., typically about 1/16 inch), an apparent bulk density of about 0.3 to about 0.5 g/cc, a pore volume of about 0.4 cc/g and a surface area of about 175 m²/g.

The preferred alumina carrier material may be prepared in any suitable manner and may be synthetically prepared or natural occurring. Whatever type of alumina is employed, it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide to a salt of aluminum such as aluminum chloride, aluminum nitrate, etc., in an amount to form an aluminum hydroxide gel which upon drying and calcinating is converted to alumina. The alumina carrier may be formed in any desired shape such as spheres, pills, cakes, extrudates, powders, granules, etc., and utilized in any desired size. For the purpose of the present invention a particularly preferred form of alumina is the sphere; and alumina spheres may be continuously manufactured by the well-known oil drop method which comprises; forming an alumina hydrosol by any of the techniques taught in the art and preferably by reacting aluminum metal with hydrochloric acid; combining the resulting hydrosol with a suitable gelling agent; and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 300° F. to about 400° F. and subjected to a calcination procedure at a temperature of about 850° F. to about 1300° F. for a period of about 1 to 20 hours. It is a good practice to subject the calcined particles to a high temperature treatment with steam in order to remove undesired acidic components such as any residual chloride. This method effects conversion of the alumina hydrogel to the corresponding crystalline gamma-alumina. See the teachings of U.S. Pat. No. 2,620,314 for additional details.

One essential constituent of the instant multimetallic catalytic composite is the Group IVA metallic component. By the use of the generic term "Group IVA metallic component" it is intended to cover the metals of Group IVA of the Periodic Table. More specifically, it is intended to cover: germanium, tin, lead, and mixtures of these metals. It is an essential feature of the present invention that substantially all of the Group IVA metallic component is present in the final catalyst in an oxidation state above that of the elemental metal. In other words, this component may be present in chemical combination with one or more of the other ingredients of the composite, or as a chemical compound of the Group IVA metal such as the oxide, sulfide, halide, oxyhalide, oxychloride, aluminate, and the like compounds. Based on the evidence currently available, it is believed that best results are obtained when substantially all of the Group IVA metallic component exists in the final composite in the form of the corresponding oxide such as the tin oxide, germanium oxide, and lead oxide, and the subsequently described oxidation and reduction steps, that are preferably used in the preparation of the instant composite, are believed to result in a catalytic composite which contains an oxide of the Group IVA metallic component. Regardless of the state in which this component exists in the composite, it can be utilized therein in any amount which is catalytically effective, with the preferred amount being about 0.01 to about 5 wt. % thereof, calculated on an elemental basis and the most preferred amount being about 0.05 to about 2 wt. %. The exact amount selected within this broad range is preferably determined as a function of the particular Group IVA metal that is utilized. For instance, in the case where this component is lead, it is preferred to select the amount of this component from the low end of this range—namely, about 0.01 to about 1 wt. %. Additionally, it is preferred to select the amount of lead as a function of the amount of the platinum group component as explained hereinafter. In the case where this component is tin, it is preferred to select from a relatively broader range of about 0.05 to about 2 wt. % thereof. And, in the preferred case, where this component is germanium, the selection can be made from the full breadth of the stated range— specifically, about 0.01 to about 5 wt. %, with best results at about 0.05 to about 2 wt. %.

This Group IVA component may be incorporated in the composite in any suitable manner known to the art to result in a uniform dispersion of the Group IVA moiety throughout the carrier material such as by physical admixture, coprecipitation or cogellation with the porous carrier materia, ion-exchange with the carrier material, or impregnation of the carrier material at any stage in its preparation. It is to be noted that it is intended to include within the scope of the present invention all conventional procedures for incorporating a metallic component in a catalytic composite, and the particular method of incorporation used is not deemed to be an essential feature of the present invention so long as the Group IVA component is uniformly distributed throughout the porous carrier material. One acceptable method of incorporating the Group IVA component into the catalytic composite involves cogelling the Group IVA component during the preparation of the preferred carrier material, alumina. This method typically involves the addition of a suitable soluble compound of the Group IVA metal of interest to the alumina hydrosol. The resulting mixture is then commingled with a suitable gelling agent, such as a relatively weak alkaline reagent, and the resulting mixture is thereafter preferably gelled by dropping into a hot oil bath as explained hereinbefore. After aging, drying, and calcining the resulting particles, there is obtained an intimate combination of the oxide of the Group IVA metal and alumina. One preferred method incorporating this component into the composite involves utilization of a soluble decomposable compound of the particular Group IVA metal of interest to impregnate the porous carrier material either before, during, or after the carrier material is calcined. In general, the solvent used during this impregnation step is selected on the basis of its capability to dissolve the desired Group IVA compound without affecting the porous carrier material which is to be impregnated; ordinarily, good results are obtained when water is the solvent; thus the preferred Group IVA compounds for use in this impregnation step are typically water-soluble and decomposable. Examples of suitable Group IVA compounds are: germanium difluoride, germanium tetra-alkoxide, germanium dioxide, germanium tetrafluoride, germanium monosulfide, tin chloride, tin bromide, tin dibromide di-iodide, tin dichloride di-iodide, tin chromate, tin difluoride tin tetraflouride, tin tetraiodide, tin sulfate, tin tartrate, lead acetate, lead bromate, lead bromide, lead chlorate, lead chloride, lead citrate, lead formate, lead lactate, lead malate, lead nitrate, lead nitrite, lead dithionate, and the like compounds. In the case where the Group IVA component is germanium, a preferred impregnation solution is germanium tetrachloride dissolved in anhydrous alcohol. In the case of tin, tin chloride dissolved in water is preferred. In the case of lead, lead nitrate dissolved in water is preferred. Regardless of which impregnation solution is utilized, the Group IVA component can be impregnated either prior to, simultaneously with, or after the other metallic components are added to the carrier material. Ordinarily, best results are obtained when this component is impregnated simultaneously with the other metallic components of the composite. Likewise, best results are ordinarily obtained when the Group IVA component is germanium oxide or tin oxide.

Regardless of which Group IVA compound is used in the preferred impregnation step, it is essential that the Group IVA metallic component be uniformly distributed throughout the carrier material. In order to achieve this objective it is necessary to maintain the pH of the impregnation solution at a relatively low level corresponding to about 7 to about 1 or less and to dilute the impregnation solution to a volume which is at least approximately the same or greater than the void volume of the carrier material which is impregnated. It is preferred to use a volume ratio of impregnation solution to void volume of carrier material of at least 1:1 and preferably about 2:1 to about 10:1 or more. Similarly, it is preferred to use a relatively long contact time during the impregnation step ranging from about ¼ hour up to about ½ hour or more before drying to remove excess solvent in order to insure a high dispersion of the Group IVA metallic component on the carrier material. The carrier material is, likewise preferably constantly agitated during this preferred impregnation step.

A second essential ingredient of the subject multimetallic catalyst is the platinum group component. Although the process of the present invention is specifically directed to the use of a catalytic composite containing platinum, it is intended to include other platinum group metals such as palladium, rhodium, ruthenium, osmium, iridium, and mixtures thereof. It is an essential feature of the present invention that substantially all of the component exist in the final catalyst in the elemental metallic state and the subsequently described reduction step is designed to accomplish this objective. Generally, the amount of the platinum group component present in the final catalyst is small compared to the quantities of the other components combined therewith, although it can be utilized in any amount which is catalytically effective. In fact, the platinum group component generally comprises about 0.01 to about 2 wt. % of the final catalytic composite, calculated on an elemental basis. Excellent results are obtained when the catalyst contains about 0.05 to about 1 wt. % of the platinum group metal. The preferred platinum group component is platinum although good results are obtained when it is palladium or iridium.

The platinum group component may be incorporated in the catalytic composite in any suitable manner known to result in a uniform dispersion of the moiety throughout the carrier material, such as coprecipitation or cogellation, ion-exchange, or impregnation. The preferred method of preparing the instant catalyst involves the utilization of a soluble, decomposable compound of a platinum group metal to impregnate the carrier material. Thus, the platinum group component may be added to the support by commingling the latter with an aqueous solution of chloroplatinic acid, Other watersoluble compounds of platinum group metals may be employed in impregnation solutions, and include ammonium chloroplatinate, bromoplatinic acid, platinum dichloride, platinum tetrachloride hydrate, platinum dichlorocarbonyl dichloride, dinitrodiaminoplatinum, palladium chloride, palladium nitrate, palladium sulfate, chloroiridic acid, and chloropalladic acid, etc. The utilization of a platinum group metal chloride compound, such as chloroplatinic acid is ordinarily preferred. Hydrogen chloride, nitric acid, or the like acid is also generally added to the impregnation solution in order to further facilitate the distribution of the metallic component throughout the carrier material. In addition, it is generally preferred to impregnate the carrier material after it has been calcined in order to minimize the risk of washing away the valuable platinum metal compounds; however, in some cases it may be advantageous to impregnate the carrier material when it is in a gelled state.

Yet another essential ingredient of the present multimetallic catalytic composite is a nickel component. This component may be present in the composite as an elemental metal, or in chemical combinations with one or more of the other ingredients of the composite, or as a chemical compound of nickel such as nickel oxide, sulfide, halide, oxychloride, aluminate, and the like. My finding is that best results are obtained when the composite contains this component in an oxidation state which is dependent on the particular Group IVA metallic component used in the instant catalyst. More specifically, when the Group IVA component is germanium, best results are achieved when substantially all of the nickel component is present in an oxidation state above that of the elemental metal. On the other hand, when the Group IVA component is tin or lead, best results are realized when the major portion or substantially all of the nickel component is present in the elemental metallic state. In other words, for the tin or lead-containing catalyst, it is important that at least 50% or more of the nickel be in the elemental state and preferably at least 60 to 90% or more. The nickel component may be utilized in the composite in any amount which is catalytically effective, with the preferred amount being about 0.01 to about 5 wt. % thereof, calculated on an elemental nickel basis. Typically, best results are obtained with about 0.05 to about 2 wt. % nickel. It is, additionally, preferred to select the specific amount of nickel from within this broad weight range as a function of the amount of the platinum group metal component, on an atomic basis, as is explained hereinafter.

The nickel component may be incorporated into the catalytic composite in any suitable manner known to those skilled in the catalyst formulation art to result in a uniform dispersion of the nickel moiety throughout the carrier material. In addition, it may be added at any stage of the preparation of the composite—either during preparation of the carrier material or thereafter—since the precise method of incorporation used is not deemed to be critical, provided the nickel component is relatively uniformly distributed throughout the carrier material. One acceptable procedure for incorporating this component into the composite involves cogelling the nickel component during the preparation of the preferred carrier material, alumina. This procedure usually comprehends the addition of a soluble, decomposable compound of nickel such as nickel chloride to the alumina hydrosol before it is gelled. The resulting mixture is then finished by conventional gelling, aging, drying, and calcination steps as explained hereinbefore. One preferred way of incorporating this component is an impregnation step wherein the porous carrier material is impregnated with a suitable nickel-containing solution either before, during, or after the carrier material is calcined. Preferred impregnation solutions are aqueous solutions of water-soluble, decomposable nickel compounds such as nickel bromate, nickel bromide, nickel perchlorate, nickel chloride, nickel fluoride, nickel iodide, nickel nitrate, nickel sulfate, and the like compounds. Best results are ordinarily obtained when the impregnation solution is an aqueous solution of nickel chloride or nickel nitrate. This nickel component can be added to the carrier material, either prior to, simultaneously with, or after the other metallic components are combined therewith.

Yet another essential ingredient of the catalyst used in the present invention is the alkali or alkaline earth component. More specifically, this component is selected from the group consisting of the compounds of the alkali metals—cesium, rubidium, potassium, sodium, and lithium—and of the alkaline earth metals—calcium, strontium, barium, and magnesium. This component exists within the catalytic composite in an oxidation state above that of the elemental metal such as a relatively stable compound such as the oxide or sulfide, or in combination with one or more of the other components of the composite, or in combination with the carrier material such as, for example, in the form of a metal aluminate. Since, as is explained hereinafter, the composite containing the alkali or alkaline earth is always calcined in an air atmosphere before use in the conversion of hydrocarbons, the most likely state this component exists in during use in the dehydrogenation reaction is the corresponding metallic oxide such as lithium oxide, potassium oxide, sodium oxide, and the like. Regardless of what precise form in which it exists in the composite, the amount of this component utilized is preferably selected to provide a composite containing about 0.1 to about 5 wt. % of the alkali or alkaline earth metal, and, more preferably, about 0.25 to about 3.5 wt. %. Best results are obtained when this component is a compound of lithium or potassium. The function of this component is to neutralize any of the acidic materials which may have been used in the preparation of the present catalyst so that the final catalyst is nonacidic.

This alkali or alkaline earth component may be combined with the porous carrier material in any manner known to those skilled in the art to result in a relatively uniform dispersion of this component throughout the carrier material with consequential neutralization of any acidic sites which may be present therein. Typically good results are obtained when it is combined by impregnation, coprecipitation, ion-exchange, and the like procedures. The preferred procedure, however, involves impregnation of the carrier material either before, during, or after it is calcined, or before, during, or after the other metallic ingredients are added to the carrier material. Best results are ordinarily obtained when this component is added to the carrier material after the other metallic components because the alkali metal or alkaline earth metal acts to neutralize the acid used in the preferred impregnation procedure for these metallic components. In fact, it is preferred to add the platinum group, nickel, and Group IVA metallic components to the carrier material, oxidize the resulting composite in an air stream at a high temperature (i.e., typically about 600 to 1000° F.), then treat the resulting oxidized composite with a mixture of air and steam in order to remove at least a portion of any residual acidity and thereafter add the alkali metal or alkaline earth component. Typically, the impregnation of the carrier material with this component is performed by contacting the carrier material with a solution of a suitable decomposable compound or salt of the desired alkali or alkaline earth metal. Hence, suitable compounds include the alkali metal or alkaline earth metal halides, sulfates, nitrates, acetates, carbonates, phosphates, and the like compounds. For example, excellent results are obtained by impregnating the carrier material after the platinum group, nickel, and Group IVA metallic components have been combined therewith, with an aqueous solution of lithium nitrate or potassium nitrate.

Regarding the preferred amounts of the various metallic components of the subject catalyst, I have found it to be a good practice to specify the amounts of the nickel component, the Group IVA metallic component, and the alkali or alkaline earth component, as a function of the amount of the platinum group component. On this basis, the amount of the nickel component is ordinarily selected so that the atomic ratio of nickel to the platinum group metal is about 0.2:1 to about 20:1, with the preferred range being about 1:1 to 10:1. Similarly, the amount of the Group IVA metallic component is ordinarily selected to produce a composite having an atomic ratio of Group IVA metal to platinum group metal within the broad range of about 0.05:1 to 10:1. However, for the Group IVA metal to platinum group metal ratio, the best practice is to select this ratio on the basis of the following preferred range for the individual species: (1) for germanium, it is about 0.3:1 to 10:1, with the most preferred range being about 0.6:1 to about 6:1; (2) for tin, it is about 0.1:1 to 3:1, with the most preferred range being about 0.5:1 to 1.5:1; and (3) for lead, it is about 0.05:1 to 0.9:1, with the most preferred range being about 0.0:1 to 0.75:1. Similarly, the amount of the alkali or alkaline earth component is ordinarily selected to produce a composite having an atomic ratio of alkali or alkaline earth metal to platinum group metal of about 5:1 to about 50:1 or more, with the preferred range being about 10:1 to about 25:1.

Another significant parameter for the instant catalyst is the "total metals content" which is defined to be the sum of the platinum group component, the nickel component, the Group IVA metallic component, and the alkali or alkaline earth component, calculated on an elemental metal basis. Good results are ordinarily obtained with the subject catalyst when this parameter is fixed at a value of about 0.2 to about 5 wt. %, with best results ordinarily achieved at a metals loading of about 0.4 to about 4 wt. %.

Integrating the above discussion of each of the essential components of the catalytic composite used in the present invention, it is evident that a particularly preferred catalytic composite comprises a combination of a platinum component, a nickel component, a Group IVA metallic component, and an alkali or alkaline earth component with an alumina carrier material in amounts sufficient to result in the composite containing from about 0.05 to about 1 wt. % platinum, group metal, about 0.05 to about 2 wt. % nickel, about 0.05 to about 2 wt. % of the Group IVA metal, and about 0.25 to about 3.5 wt. % of the alkali or alkaline earth metal.

Regardless of the details of how the components of the catalyst are combined with the porous carrier material, the resulting multimetallic composite generally will be dried at a temperature of about 200° F. to about 600° F. for a period of from about 2 to 24 hours or more, and finally calcined or oxidized at a temperature of about 600° F. to about 1100° F. in an air atmosphere for a period of about 0.5 to 10 hours, preferably about 1 to about 5 hours, in order to convert substantially all the metallic components to the corresponding oxide form. When acidic components are present in any of the reagents used to effect incorporation of any one of the components of the subject composite, it is a good practice to subject the resulting oxidized composite to a high temperature treatment with steam or with a mixture of steam and air, either after or before the calcination step described above, in order to remove as much as possible of the undesired acidic component. For example, when the platinum group component is incorporated by impregnating the carrier material with chloroplatinic acid, it is preferred to subject the resulting composite to a high temperature treatment with steam in order to remove as much as possible of the undesired chloride.

It is preferred that the resultant oxidized multimetallic calcined catalytic composite be subjected to a substantially water-free reduction step prior to its use in the conversion of hydrocarbons. This step is designed to insure a uniform and finely divided dispersion of the metallic components throughout the carrier material. Preferably, substantially pure and dry hydrogen (i.e., less than 20 vol. ppm. $H_2O$) is used as the reducing agent in this step. The reducing agent is contacted with the oxidized composite at a temperature of about 800° F. to about 1200° F., a gas hourly space velocity of about 100 to about 5,000 hr.$^{-1}$, and for a period of time of about 0.5 to 10 hours or more, effective to reduce at least substantially all the platinum group component to the elemental metallic state while maintaining the Group IVA component in a positive oxidation state. This reduction treatment may be performed in situ as part of a start-up sequence if precautions are taken to predry the plant to a substantially water-free state and if substantially water-free hydrogen is used.

The resulting reduced multimetallic catalytic composite may, in some cases, be beneficially subjected to a presulfiding operation designed to incorporate in the catalytic composite from about 0.05 to about 0.5 wt. % sulfur calculated on an elemental basis. Preferably, this presulfiding treatment takes place in the presence of hydrogen and a suitable decomposable sulfur-containing compound such as hydrogen sulfide, lower molecular weight mercaptans, organic sulfides, etc. Typically, this procedure comprises treating the reduced catalyst with a sulfiding gas such as a mixture containing a mole ratio of $H_2$ to $H_2S$ of about 10:1 at conditions sufficient to effect the desired incorporation of sulfur, generally including a temperature ranging from about 50°F. up to about 1100°F. or more. This presulfiding step can be performed in situ or ex-situ.

According to the method of the present invention, the dehydrogenatable hydrocarbon is contacted with the instant multimetallic catalytic composite in a dehydrogenation zone at dehydrogenation conditions. This contacting may be accomplished by using the catalyst in a fixed bed system, a moving bed system, a fluidized bed system, or a batch type operation; however, in view of the danger of attrition losses of the valuable catalyst and of well-known operation advatages, it is preferred to use a fixed bed system. In this system, the hydrocarbon feed stream is preheated by any suitable heating means to the desired reaction temperature and then passed into a dehydrogenation zone containing a fixed bed of the catalyst type previously characterized. It is, of course, understood that the dehydrogenation zone may be one or more separate reactors with suitable heating means therebetween to insure that the desired conversion temperature is maintained at the entrance to each reactor. It is also to be noted that the reactants may be contacted with the catalyst bed in either upward, downward, or radial flow fashion, with the latter being preferred. In addition, it is to be noted that the reactants may be in the liquid phase, a mixed liquid-vapor phase, or a vapor phase when they contact the catalyst, with best results obtained in the vapor phase.

Although hydrogen is the preferred diluent for use in the subject dehydrogenation method, in some cases other art-recognized diluents may be advantageously utilized such as steam, methane, carbon dioxide, and the like diluents. Hydrogen is preferred because it serves the dual-function of not only lowering the partial pressure of the dehydrogenatably hydrocarbon, but also of suppressing the formation of hydrogen-deficient, carbonaceous deposits on the catalytic composite. Ordinarily, hydrogen is utilized in amounts sufficient to insure a hydrogen to hydrocarbon mole ratio of about 1:1 to about 20:1, with best results obtained in the range of about 1.5:1 to about 10:1. The hydrogen stream charged to the dehydrogenation zone will typically be recycle hydrogen obtained from the effluent stream from this zone after a suitable separation step.

When hydrogen is used as the diluent, an essential feature of the present invention is to add water or a water-producing substance to the dehydrogenation zone. This water additive may be included in the charge stock, or in the hydrogen stream, or in both of these, or added independently of these. Ordinarily, it is preferred to inject the necessary water by saturating at least a portion of the input hydrogen stream with water. Good results are also obtained when a water-producing compound such as a $C_2$ to $C_8$ alcohol, ether, ketone, aldehyde, or the like oxygen-containing organic compound is added to the charge stock. Regardless of the source of the water, the amount of equivalent water added should be sufficient to maintain the total amount of water continuously entering the dehydrogenation zone in the range of about 50 to about 10,000 wt. ppm. of the hydrocarbon charge stock, with best results obtained at a level corresponding to about 1500 to 5000 wt. ppm. of the hydrocarbon charge stock.

Concerning the conditions utilized in the process of the present invention, these are generally selected from the conditions well known to those skilled in the art for the particular dehydrogenatable hydrocarbon which is charged to the process. More specifically, suitable conversion temperatures are selected from the range of about 700 to about 1200°F., with a value being selected from the lower portion of this range for the more easily dehydrogenated hydrocarbons such as the long chain normal paraffins and from the higher portion of this range for the more difficultly dehydrogenated hydrocarbons such as propane, butane, and the like hydrocarbons. For example, for the dehydrogenation of $C_6$ to $C_{30}$ normal paraffins, best results are ordinarily obtained at a temperature of about 800° to about 950° F. The pressure utilized is ordinarily selected at a value which is as low as possible consistent with the maintenance of catalyst stability, and is usually about 0.1 to about 10 atmospheres, with best results ordinarily obtained in the range of about 0.5 to about 3 atmospheres. In addition, a liquid hourly space velocity (calculated on the basis of the volume amount, as a liquid, of hydrocarbon charged to the dehydrogenation zone per hour divided by the volume of the catalyst bed utilized) is selected from the range of about 1 to about 40 hr.$^{-1}$, with best results for the dehydrogenation of long chain normal paraffins typically obtained at a relatively high space velocity of about 25 to 35 hr.$^{-1}$.

Regardless of the details concerning the operation of the dehydrogenation step, an effluent stream will be withdrawn therefrom. This effluent will contain unconverted dehydrogenatable hydrocarbons, hydrogen, and products of the dehydrogenation reaction. This stream is typically cooled and passed to a separating zone wherein a hydrogen-rich vapor phase is allowed to separate from a hydrocarbon-rich liquid phase. In general, it is usually desired to recover the unreacted dehydrogenatable hydrocarbon from this hydrocarbon-rich liquid phase in order to make the dehydrogenation process economically attractive. This recovery step can be accomplished in any suitable manner known to the art such as by passing the hydrocarbon-rich liquid phase through a bed of suitable adsorbent material which has the capability to selectively retain the dehydrogenated hydrocarbons contained therein or by contacting same with a solvent having a high selectivity for the dehydrogenated hydrocarbon or by a suitable fractionation scheme where feasible. In the case where the dehydrogenated hydrocarbon is a mono-olefin, suitable adsorbents having this capability are activated silica gel, activated carbon, activated alumina, various types of specially prepared molecular sieves, and the like adsorbents. In another typical case, the dehydrogenated hydrocarbons can be separated from the unconverted dehydrogenatably hydrocarbons by utilizing the inherent capability of the dehydrogenated hydrocarbons to enter into several well-known chemical reactions such as alkylation, oligomerization, halogenation, sulfonation, hydration, oxidation, and the like reactions. Irrespective of how the dehydrogenated hydrocarbons are separated from the unreacted hydrocarbons, a stream containing the unreacted dehydrogenatably hydrocarbons will typically be recovered from this hydrocarbon separation step and recycled to the dehydrogenation step. Likewise, the hydrogen phase present in the hydrogen separating zone will be withdrawn therefrom, a portion of it vented from the system in order to remofe the net hydrogen make, and the remaining portion is typically recycled, through suitably compressing means, to the hydrogenation step in order to provide diluent hydrogen therefor.

In a preferred embodiment of the present invention wherein long chain normal paraffin hydrocarbons are dehydrogenated to the corresponding normal monoolefins, a preferred mode of operation of this hydrocarbon separation step involves an alkylation reaction. In this mode, the hydrocarbon-rich liquid phase withdrawn from the separating zone is combined with a stream containing an alkylatable aromatic and the resulting mixture passed to an alkylation zone containing a suitable highly acidic catalyst such as an anhydrous solution of hydrogen fluoride. In the alkylation zone the mono-olefins react with the alkylatable aromatic while the unconverted normal paraffins remain substantially unchanged. The effluent stream from the alkylation zone can then be easily separated, typically by means of a suitable fractionation system, to allow recovery of the unreacted normal paraffins. The resulting stream of unconverted normal paraffins is then usually recycled to the dehydrogenation step of the present invention.

The following working examples are introduced to illustrate further the novelty, mode of operation, utility and benefits associated with the dehydrogenation method and multimetallic catalytic composite of the present invention. These examples are intended to be illustrative rather than restrictive.

These examples are all performed in a laboratory scale dehydrogenation plant comprising a reactor, a hydrogen separating zone, a heating means, cooling means, pumping means, compressing means, and the like equipment. In this plant the hydrocarbon feed stream containing the dehydrogenatable hydrocarbon is combined with a hydrogen stream containing water in an amount corresponding to about 2000 wt. ppm. of the hydrocarbon feed, and the resultant mixture heated to the desired conversion temperature, which refers herein to the temperature maintained at the inlet to the reactor. The heated mixture is then passed into contact with the catalyst which is maintained as a fixed bed of catalyst particles in the reactor. The pressures reported herein are recorded at the outlet from the reactor. An effluent stream is withdrawn from the reactor, cooled, and passed into the separating zone wherein a hydrogen gas phase separates from a hydrocarbonrich liquid phase containing dehydrogenated hydrocarbons, unconverted dehydrogenatable hydrocarbons and a minor amount of side products of the dehydrogenation reaction. A portion of the hydrogen-rich gas phase is recovered as excess recycle gas with the remaining portion being continuously withdrawn, admixed with the requisite amount of water, and recycled through suitable compressive means to the heating zone as described above. The hydrocarbon-rich liquid phase from the separating zone is withdrawn therefrom and subjected to analysis to determine conversion and selectivity for the desired dehydrogenated hydrocarbon as will be indicated in the examples. Conversion numbers of the dehydrogenatable hydrocarbon reported herein are all calculated on the basis of disappearance of the dehydrogenatable hydrocarbon and are expressed in mole percent. Similarly, selectivity numbers are reported on the basis of moles of desired hydrocarbon produced per 100 moles of dehydrogenatable hydrocarbon converted.

All of the catalysts utilized in these examples are prepared according to the following general method with suitable modifications in stoichiometry to achieve the compositions reported in each example. First, an alumina carrier material comprising 1/16 inch spheres is prepared by: forming an aluminum hydroxyl chloride sol by dissolving substantially pure aluminum pellets in a hydrochloric acid solution, adding hexamethylenetetramine to the sol, gelling the resulting solution by dropping it into an oil bath to form spherical particles of an alumina hydrogel, aging, and washing the resulting particles with an ammoniacal solution, and finally drying, calcining, and steaming the aged and washed particles to form spherical particles of gamma-alumina containing substantially less than 0.1 wt. % combined chloride. Additional details as to this method of preparing this alumina carrier material are given in the teachings of U.S. Pat. No. 2,620,314.

Second, a measured amount of germanium tetrachloride is dissolved in anhydrous ethanol. The resulting solution is aged at room temperature until an aquilibrium condition is established therein. An aqueous solution containing chloroplatinic acid, nickel nitrate, and nitric acid is also prepared. The two solutions are then intimately admixed and used to impregnate the gamma-alumina particles. The amounts of the various reagents are carefully selected to yield final catalytic composites containing the required amounts of platinum, nickel, and germanium. In order to insure uniform distribution of metallic components throughout the carrier material, this impregnation step is performed by adding the alumina particles to the impregnation mixture with constant agitation. The impregnation mixture is maintained in contact with the alumina particles for a period of about ½ hour at a temperature of 70° F. thereafter, the temperature of the impregnation mixture is raised to about 225° F. and the excess solution is evaporated in a period of about 1 hour. The resulting dried particles are then subjected to a calcination or oxidation treatment in an air atmosphere at a temperature of about 500° to about 1000° F. for about 2 to 10 hours effective to convert the metallic components to the corresponding oxides. Thereafter, the resulting calcined particles are treated with an air stream containing from about 10 to about 30% steam at a temperature of about 800° to about 1000° F. for an additional period from about 1 to about 5 hours in order to further reduce the residual combined chloride in the composite.

Finally, the alkali or alkaline earth metal component is added to the resulting calcined particles in a second impregnating step. This second impregnation step involves contacting the calcined particles with an aqueous solution of a suitable decomposable salt of the desired alkali or alkaline earth component. For the composite utilized in the present examples, the salt is either lithium nitrate or potassium nitrate. The amount of this salt is carefully chosen to result in a final composite having the desired composition. The resulting alkali impregnated particles are then dried, calcined, and steamed in exactly the same manner as described above following the first impregnation step.

In all the examples the catalyst is reduced during start-up by contacting with hydrogen at an elevated temperature of about 900 to 1100° F. for a period of time sufficient to reduce substantially all of the platinum component to the elemental state while maintaining the other components in a positive oxidation state. Thereafter, the composite is sulfided with a mixture of $H_2$ and $H_2S$ as explained hereinbefore.

EXAMPLE I

The reactor is loaded with 100 cc's of a catalyst containing, on an elemental basis, 0.375 wt. % platinum, 0.5 wt. % nickel, 0.25 wt. % germanium, 0.5 wt. % lithium, and less than 0.15 wt. % chloride. The feed stream utilized is commerical grade isobutane containing 99.7 wt. % isobutane and 0.3 wt. % normal butane. The feed stream is contacted with the catalyst at a temperature of 1065° F., a pressure of 10 psig., a liquid hourly space velocity of 4.0 hr.$^{-1}$, and a hydrogen to hydrocarbon mole ratio of 2:1. The dehydrogenation plant is lined-out at these conditions and a 20 hour test period commenced. The hydrocarbon product stream from the plant is continuously analyzed by GLC (gas-liquid chromotography) and a high conversion of isobutane is observed with good selectivity for isobutylene.

EXAMPLE II

The catalyst contains, on an elemental basis, 0.375 wt. % platinum, 0.5 wt. % germanium, 0.25 wt. % nickel, 0.5 wt. % lithium, and less than 0.15 wt. % combined chloride. The feed stream is commercial grade normal dodecane. The dehydrogenation reactor is operated at a temperature of 870° F., a pressure of 10 psig., a liquid hourly space velocity of 32 hr.$^{-1}$, and a hydrogen to hydrocarbon mole ratio of 8:1. After a line-out period, a 20 hour test period is performed during which the average conversion of the normal dodecane is maintained at a high level with a selectivity for dodecane of substantially about 90%.

EXAMPLE III

The catalyst is the same as utilized in Example II. The feed stream is normal tetradecane. The conditions utilized are a temperature of 840° F., a pressure of 20 psig., a liquid hourly space velocity of 32 hr.$^{-1}$, and a hydrogen to hydrocarbon mole ratio of 8:1. After a line-out period, a 20 hour test shows an average conversion of approximately 12% and a selectivity for tetradecene of above about 95%.

EXAMPLE IV

The catalyst contains, on an elemental basis, 0.6 wt. % platinum, 0.2 wt. % nickel, 0.5 wt. % germanium, and 0.6 wt. % lithium, with combined chloride being less than 0.2 wt. %. The feed stream is substantially pure normal butane. The conditions utilized are a temperature of 950° F., a pressure of 15 psig., a liquid hourly space velocity of 4.0 hr.$^{-1}$, and a hydrogen to hydrocarbon mole ratio of 4:1. After a line-out period, a 20 hour test is performed and excellent conversion of the normal butane to butene is observed.

EXAMPLE V

The catalyst contains, on an elemental basis, 0.375 wt. % platinum, 0.375 wt. % nickel, 0.5 wt. % germanium, 2.8 wt. % potassium, and less than 0.2 wt. % combined chloride. The feed stream is commercial grade ethylbenzene. The conditions utilized are a pressure of 15 psig., a liquid hourly space velocity of 32 hr.$^{-1}$, a temperature of 950° F., and a hydrogen to hydrocarbon mole ratio of 8:1. During a 20 hour test period, at least 85% of equilibrium conversion of ethylbenzene is observed with high selectivity for styrene.

It is intended to cover by the following claims all changes and modifications of the above disclosure of the present invention that would be self-evident to a man of ordinary skill in the catalyst formulation art or in the hydrocarbon dehydrogenation art.

I claim as my invention:

1. A method for dehydrogenating a dehydrogenatable hydrocarbon comprising contacting the hydrocarbon, hydrogen, and water or water-producing substance, at dehydrogenation conditions, with a non-acidic catalytic composite comprising a porous carrier material containing, on an elemental basis, about 0.01 to about 2 wt. % platinum group metal, about 0.01 to about 5 wt. % nickel, about 0.01 to about 5 wt. Group IVA metal, and about 0.1 to about 5 wt. % of an alkali or alkaline earth metal, wherein the platinum group metal, Group IVA metal, nickel, and alkali or alkaline earth metal are uniformly dispersed throughout the porous carrier material, wherein substantially all of the platinum group metal is present in the elemental metallic state, wherein substantially all of the Group IVA metal is present in an oxidation state above that of the elemental metal and wherein substantially all of the alkali or alkaline earth metal is present in an oxidation state above that of the elemental metal.

2. A method as defined in claim 1 wherein the platinum group metal is platinum.

3. A method as defined in claim 1 wherein the platinum group metal is palladium.

4. A method as defined in claim 1 wherein the porous carrier material is a refractory inorganic oxide.

5. A method as defined in claim 4 wherein the refractory inorganic oxide is alumina.

6. A method as defined in claim 1 wherein the alkali or alkaline earth metal is lithium.

7. A method as defined in claim 1 wherein the alkali or alkaline earth metal is potassium.

8. A method as defined in claim 1 wherein substantially all of the nickel is present in the elemental metallic state.

9. A method as defined in claim 1 wherein the Group IVA metal is germanium.

10. A method as defined in claim 1 wherein the Group IVA metal is tin.

11. A method as defined in claim 1 wherein the Group IVA metal is lead.

12. A method as defined in claim 1 wherein the atomic ratio of Group IVA metal to platinum group metal is about 0.05:1 to about 10:1, wherein the atomic ratio of nickel to platinum group metal is about 0.2:1 to about 20:1 and wherein the atomic ratio of the alkali or alkaline earth metal to platinum group metal is about 5:1 to 50:1.

13. A method as defined in claim 1 wherein the composite contains about 0.05 to about 0.5 wt. % sulfur, calculated on an elemental basis.

14. A method as defined in claim 9 wherein substantially all of the germanium is present as germanium oxide.

15. A method as defined in claim 10 wherein substantially all of the tin is present as tin oxide.

16. A method as defined in claim 11 wherein substantially all of the lead is present as lead oxide.

17. A method as defined in claim 1 wherein the composite contains, on an elemental basis, about 0.05 to about 1 wt. % platinum group metal, about 0.05 to about 2 wt. % nickel, about 0.05 to about 2 wt. % Group IVA metal, and about 0.25 to about 3.5 wt. % alkali or alkaline earth metal and wherein the porous carrier material is alumina.

18. A method as defined in claim 1 wherein the dehydrogenatable hydrocarbon is an aliphatic compound containing 2 to 30 carbon atoms per molecule.

19. A method as defined in claim 1 wherein the dehydrogenatable hydrocarbon is a normal paraffin hydrocarbon containing about 4 to 30 carbon atoms per molecule.

20. A method as defined in claim 1 wherein the dehydrogenatable hydrocarbon is a normal paraffin hydrocarbon containing about 10 to 18 carbon atoms per molecule.

21. A method as defined in claim 1 wherein the dehydrogenatable hydrocarbon is an alkylaromatic, the alkyl group of which contains 2 to 6 carbon atoms.

22. A method as defined in claim 1 wherein the dehydrogenatable hydrocarbon is a naphthene.

23. A method as defined in claim 1 wherein the dehydrogenation conditions include a temperature of about 700° to about 1200° F., a pressure of about 0.1 to about 10 atmospheres, a liquid hourly space velocity of about 1 to 40 hr.$^{-1}$ and a hydrogen to hydrocarbon mole ratio of about 1:1 to about 20:1.

24. A method as defined in claim 1 wherein the amount of water or water-producing substance used therein corresponds to about 50 to about 10,000 wt. ppm. of the hydrocarbon charge.

* * * * *